United States Patent [19]

Ohleyer

[11] Patent Number: 5,422,257
[45] Date of Patent: Jun. 6, 1995

[54] METHOD FOR OBTAINING POLY-β-HYDROXYOCTANOIC ACID VIA SOLVENT EXTRACTION

[75] Inventor: Eric Ohleyer, Cruseiles, France

[73] Assignee: Firmenich SA, Geneva, Switzerland

[21] Appl. No.: 94,198

[22] PCT Filed: Nov. 13, 1992

[86] PCT No.: PCT/EP92/02608

§ 371 Date: Jul. 26, 1993

§ 102(e) Date: Jul. 26, 1993

[87] PCT Pub. No.: WO93/11656

PCT Pub. Date: Jun. 10, 1993

[30] Foreign Application Priority Data

Nov. 29, 1991 [CH] Switzerland ............... 3506/91

[51] Int. Cl.$^6$ ............... C12P 7/62; C12P 7/42
[52] U.S. Cl. ............... 435/135; 435/146
[58] Field of Search ............... 435/135, 146

[56] References Cited

U.S. PATENT DOCUMENTS

| | | | |
|---|---|---|---|
| 3,275,610 | 9/1966 | Coty | 526/199 |
| 4,140,741 | 2/1979 | Lafferty et al. | 264/184 |
| 4,968,611 | 11/1990 | Traussnig et al. | 435/146 |

FOREIGN PATENT DOCUMENTS

| | | |
|---|---|---|
| 0124309 | 11/1984 | European Pat. Off. |
| 3143397 | 6/1991 | Japan |
| 9012104 | 10/1990 | WIPO |

OTHER PUBLICATIONS

Haywood et al., "Accumulation of a Polyhydroxyalkanoth-containing Primarily 3-hydroxydicanrth from Sample Carbohydrate Substrates by Pseudomas" pp. strain NCIMP 40135; Chemical Abstracts, 114:20781f, 1991.

Kirk-Othmer, "Acetone", pp. 176–194, Kirk-Othmer Encyclopedia of Chemical Technology, Pub: John Wiley and Sons, 1978.

Kirk-Othmer, "Ethus", pp. 866–876, Kirk-Othmer Encyclopedia of Chemical Technology, Pub: John Wiley and Sons, 1978.

*Primary Examiner*—Marian C. Knode
*Assistant Examiner*—Francisco C. Prats
*Attorney, Agent, or Firm*—Pennie & Edmonds

[57] ABSTRACT

Poly-β-hydroxyoctanoic acid, a multi-purpose product, is prepared by means of a method for aerobically fermenting bacteria which can accumulate said acid, wherein a nutrient solution containing a growth control agent is added to the culture medium to maintain a dilution level of about 0.050–0.100 h$^{-1}$. Once it has been separated from the culture medium, the biomass is suspended in acetone or isopropanol, and the separated and dried cell mass is dissolved in an unchlorinated inert organic solvent. The desired acid is obtained by evaporating the clear filtrate which is recovered after separating the solid mass in the form of a stable polymeric film.

7 Claims, No Drawings

METHOD FOR OBTAINING POLY-β-HYDROXYOCTANOIC ACID VIA SOLVENT EXTRACTION

TECHNICAL FIELD

The invention relates to the field of organic synthesis. In particular, it has as its object a novel process for the preparation of poly-β-hydroxyoctanoic acid, a polymer formed of repeating units of formula

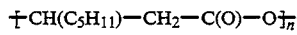

$$\pm CH(C_5H_{11})-CH_2-C(O)-O\pm_n$$

which process allows the preparation of said acid in good yields and without significant degradation of the polymer.

The process of the invention is based on a method of extraction of poly-β-hydroxyoctanoic acid from a culture of bacteria containing it, by means of an organic solvent.

PRIOR ART

The poly-hydroxyalkanoic acids are storage compounds which can be found in certain families of bacteria. These acids deposit themselves in aggregate form in the cytoplasmic solution when the cells are grown in a carbon-rich medium and wherein one of the nutrients is growth-limiting.

Several methods of extraction of these acids have been described in the literature. They concern most particularly the production of poly-β-hydroxybutanoic acid or of poly-β-hydroxyoctanoic acid for which there has been suggested an extraction by means of chlorinated solvents, for example chloroform or methylene chloride, starting from cells obtained via cold-drying, more specifically by lyophilization. Examples of such methods are described in *Appl. Environ. Microbiol.*, 55 (1989), 1949; *Appl. Environ. Microbiol.*, 54 (1988), 1977 and Appl. Environ. Microbiol., 45 (1983), 71.

The use of chlorinated solvents on the lyophilized biomass comes up against two major inconvenients. On the one hand, such solvents are to be avoided, as much as possible, in large scale industrial operations for obvious reasons of protection of the environment, and, on the other hand, the lyophilization process is particularly expensive.

DESCRIPTION OF THE INVENTION

The present inventions brings a novel solution to this problem. In its general principle, the process of the invention consists in growing appropriate bacteria in an adequate nutrient medium. The bacteria are subsequently separated, after fermentation, by the usual techniques, for example centrifugation, and the wet biomass thus obtained is suspended in acetone or isopropanol or any other dehydrating solvent known from the prior art. Thus, after separation, the still wet biomass is stirred in the chosen suspension organic solvent until an homogeneous suspension is obtained. The separation of the solid cellular mass from the suspension is carried out by the usual methods, for example decantation, filtration or centrifugation. Simple filtration by means of a Büchner filter allows the separation of the bacteria cells in the form of an already dry powder. A subsequent drying can be optionally carried out by direct exposure to air of the separated solid.

It should be noted that, although poly-β-hydroxyoctanoic acid is completely soluble in anhydrous acetone, the presence of water, even in very small quantities, renders the polymer quite insoluble.

The extraction of poly-β-hydroxyoctanoic acid takes place in nonchlorinated organic solvents defined by the following group: acetone, methylisobutylketone, diisopropylketone, diethylketone, ethyl acetate, propyl acetate, butyl acetate, diethyl ether, diisopropyl ether and tetrahydrofuran. Preferably, acetone or tetrahydrofuran are used. In the absence of water, these solvents make it possible to completely dissolve the polymer obtained by simple stirring at room temperature. The relative proportion of the mass of dried cells with regard to acetone or tetrahydrofuran is comprised between about 7.5 and 15% (weight/volume).

By filtration of the obtained suspension and evaporation of the separated clear solution, the desired product is finally obtained in the form of a translucent polymeric film, consisting essentially of poly-β-hydroxyoctanoic acid.

As indicated above, the intracellular formation of poly-β-hydroxyalkanoic acids has been observed in a great number of bacteria families. In particular, fermentation of bacteria of the *Pseudomonas* genus, in a nutrient medium wherein one of the agents is growth-limiting, gives rise to the formation of poly-β-hydroxyoctanoic acid. Such bacteria cultures can be obtained at depositories such as the ATCC (American Type Culture Collection, Rockville, Md., U.S.A.) or the DSM (Deutsche Sammlung von Mikroorganismen, Göttingen, Germany). Specifically, in the process of the invention, bacteria from one of the following strains were used:

*Pseudomonas oleovorans* ATCC 29347,
*Pseudomonas sp.* DSM 1650, and
*Pseudomonas citronellonis* DSM 50332.

We observed that, when the fermentation was carried out according to a continuous culture mode, for example chemostat, by addition of the solution of the nutrient agent to the fermentation medium, the rate of dilution has a determining influence on the yields of poly-β-hydroxyoctanoic acid formed. Thus, at dilution rates comprised between about 0.050 and 0.100 h$^{-1}$, the acid in question was obtained at the rate of 14–21 parts by weight for 100 parts of dry cellular mass. This yield decreases rapidly at higher dilution rates, an unexpected phenomenon for which we have no satisfactory explanation.

The invention thus also relates to a process for obtaining poly-β-hydroxyoctanoic acid by aerobic fermentation of bacteria capable of accumulating said acid when grown in a carbon-rich nutrient solution and wherein one of the nutrient agents is growth-limiting, characterized in that the nutrient solution is added to the culture in such a way as to maintain the dilution rate comprised between about 0.050 and 0.100 h$^{-1}$, in that the biomass is then separated from the culture medium, in that the separated biomass is suspended in acetone or isopropanol or any other known dehydrating solvent, in that the obtained suspension is filtered and the solid dried biomass is put into contact with an inert organic solvent chosen in the following group:

acetone, methylisobutylketone, diisopropylketone, diethylketone, ethyl acetate, propyl acetate, butyl acetate, diethyl ether, diisopropyl ether and tetrahydrofuran, in that the solid mass is separated from the obtained suspension and, finally, the resulting clear solution is evaporated.

The invention is illustrated in a more detailed manner by way of the following examples, wherein the temperatures are indicated in degrees centigrade and the abbreviations have the usual meaning in the art.

EXAMPLE 1

The particular fermentation conditions applied in this example are analogous to those described in the literature. However, as will be described further on, the reaction is carried out under steady state conditions, thus with a constant biomass concentration.

Bacteria of the *Pseudomonas sp.* DSM 1650 strain were grown under aerobic conditions adjusting the pH to 7.0 and the temperature to 32°. The fermentation was carried out in a 2 l chemostat in a growth-limiting nitrogenous medium, the composition of which was the following (proportions expressed relative to 1 l of distilled water).

| octanoic acid | 15.12 g |
|---|---|
| NH$_4$Cl | 1.75 g |
| K$_2$HPO$_4$ | 4.40 g |
| KH$_2$PO$_4$ | 3.40 g |
| MgSO$_4$.7H$_2$O | 2.70 g |
| Na$_2$SO$_4$ | 2.00 g |
| oligo-elements solution in HCl* | 2.5 ml |

*this solution had the following composition (proportions expressed relative to 1 l of HCl 1N):

| | [g] |
|---|---|
| FeSO$_4$.7H$_2$O | 2.78 |
| MnCl$_2$.4H$_2$O | 1.98 |
| CoSO$_4$.7H$_2$O | 2.81 |
| CaCl$_2$.2H$_2$O | 1.67 |
| CuSO$_4$.5H$_2$O | 0.14 |
| ZnSO$_4$.7H$_2$O | 0.29 |

This nutritive solution was added to the fermentation medium in such a way as to maintain the dilution rate at a value of 0.085 h$^{-1}$.

After having reached a steady state, i.e. a constant biomass concentration and a complete consumption of carbon and nitrogen, the cellular mass is stored in a reservoir before centrifugation (30 min), washed with demineralized water and again centrifuged.

The wet mass (51.5 g) harvested from 2 l of culture was suspended in 250 ml of isopropanol and stirred at room temperature until obtaining an homogeneous suspension, then filtered by means of a Büchner type filter and 12.4 g of dry cellular mass were obtained after air-drying.

This dried mass was suspended in 155 ml of acetone and stirred during 1 h at room temperature, then it was filtered.

The clear filtrate was then evaporated under air to yield 2.43 g of a translucent polymeric film. The content of the cellular mass in polymer was determined by gas chromatography of the β-hydroxyoctanoic acid methyl ester obtained by methanolysis of the polymer [see for example Appl. Environ. Microbiol. 54 (1988), 1977]. The proportion of polymer reached 20% by weight.

EXAMPLE 2

A dried biomass was obtained following the method described in the previous example.

12.6 g of this biomass were suspended in 126 ml of acetone and stirred 3 h at room temperature, then the suspension was filtered. The clear filtrate was evaporated under reduced pressure at a temperature which did not go over 40° and 2.63 g of polymer were thus recovered. The molecular weight of the polymer was calculated through the following formula:

$$MW = 2.11 \cdot 10^2 \cdot [\eta]^{1/0.74}$$

according to Makromolekulare Chemie 176 (1975), 2655, wherein MW represents the molecular weight and [η] defines the intrinsic viscosity as measured at 30° by a Brookfield digital viscosimeter. The polymer was solubilised at different concentrations in cyclohexanone.

Other experiments were carried out by suspending the dried biomass in solvents other than acetone, for example methylisobutylketone, diisopropylketone, diethylketone, ethyl acetate, propyl acetate, butyl acetate, diethyl ether or yet diisopropyl ether.

Similar results were also obtained by fermentation of other strains than *Pseudomonas sp.* DSM 1650. Thus *Pseudomonas oleovorans* ATCC 29347 and *Pseudomonas citronellonis* DSM 50332 were used.

EXAMPLE 3

A dried biomass was obtained according to the method described in Example 1. The nutritive solution had the following composition (proportions expressed relative to 1 l disfilled water).

| octanoic acid | 15.12 g |
|---|---|
| NH$_4$Cl | 1.92 g |
| K$_2$HPO$_4$ | 4.40 g |
| KH$_2$PO$_4$ | 3.40 g |
| MgSO$_4$.7H$_2$O | 1.50 g |
| Na$_2$SO$_4$ | 2.00 g |
| oligo-elements solution in HCl* | 5.0 ml |

*this solution had the following composition (proportions expressed relative to 1 l of HCl 1N):

| | [g] |
|---|---|
| FeSO$_4$.7H$_2$O | 2.78 |
| MnCl$_2$.4H$_2$O | 1.98 |
| CoSO$_4$.7H$_2$O | 2.81 |
| CaCl$_2$.2H$_2$O | 1.67 |
| CuSO$_4$.5H$_2$O | 0.14 |
| ZnSO$_4$.7H$_2$O | 0.29 |

It was operated as indicated in Example 1 by adding the nutrient solution to the fermentation medium such as to maintain the dilution rate at the value indicated in the following table. Poly-β-hydroxyoctanoic acid was thus obtained in the proportions indicated, expressed as content of polymer in the cellular mass.

| D$^{(1)}$ [h$^{-1}$]: | 0.050 | 0.085 | 0.100 | 0.135 | 0.200 |
|---|---|---|---|---|---|
| PHO [%]$^{(2)}$ | 14 | 21 | 16 | 7 | ~1% |

$^{(1)}$dilution rate
$^{(2)}$poly-β-hydroxyoctanoic add [parts by weight]

I claim:

1. A process for obtaining poly-β-hydroxyoctanoic acid by extraction with an organic solvent of a biomass containing said acid and obtained by fermentation of bacteria of the *Pseudomonas* genus under aerobic conditions in a carbon-rich medium and wherein one of the nutrients is growth-limiting, said process comprising the steps of contacting the biomass, in precedingly dried form, with an inert organic solvent of acetone, methylisobutylketone, diisopropylketone, diethylketone, ethyl acetate, propyl acetate, butyl acetate, diethyl ether, diisopropyl ether, or tetrahydrofuran to form a suspension; separating the solid mass from the obtained suspension to form a clear solution; and evaporating the clear solution to obtain the poly-β-hydroxyoctanoic acid.

2. The process according to claim 1, wherein the proportion of dried biomass relative to acetone is between about 7.5 and 15% (weight/volume).

3. The process according to claim 1, wherein the proportion of dried biomass relative to tetrahydrofuran is between about 7.5 and 15% (weight/volume).

4. The process according to claim 1 wherein the biomass is obtained by fermentation of bacteria belonging to one of the following strains:
   *Pseudomonas oleovorans* ATCC 29347,
   *Pseudomonas sp.* DSM 1650, and
   *Pseudomonas citronellonis* DSM 50332.

5. The process according to claim 1, wherein the biomass is formed of a dried cellular mass obtained by addition of acetone or isopropanol to a wet cellular mass, followed by filtration and drying to air of the separated solid mass.

6. A process for obtaining poly-β-hydroxyoctanoic acid by aerobic fermentation of bacteria of the *Pseudomonas* genus capable of accumulating said acid when cultivated in a carbon-rich nutritive solution and wherein one of the nutrients is growth-limiting, said process comprising the steps of adding the nutritive solution to a culture of the bacteria to maintain a dilution rate between about 0.050 and 0.100 $h^{-1}$; separating the biomass from the culture medium; suspending the separated biomass in acetone or isopropanol to form a suspension; filtering and drying the suspension to obtain a dried biomass; contacting the dried biomass with an inert organic solvent of acetone, methylisobutylketone, diisopropylketone, diethylketone, ethyl acetate, propyl acetate, butyl acetate, diethyl ether, diisopropyl ether, or tetrahydrofuran, to form a suspension; separating the solid mass from the suspension to form a clear solution; and evaporating the resulting clear solution to obtain the poly-β-hydroxyoctanoic acid.

7. In a process for obtaining poly-β-hydroxyoctanoic acid by aerobic fermentation of bacteria of the *Pseudomonas* genus which comprises:
   adding a carbon-rich nutritive solution wherein one of the nutrients is growth-limiting to a culture of the bacteria capable of accumulating said acid to maintain a dilution rate between about 0.050 and 0.100 $h^{-1}$ to form a biomass containing poly-β-hydroxyoctanoic acid,
   separating the biomass from the culture,
   suspending the separated biomass in acetone or isopropanol,
   filtering and drying the suspended biomass,
   treating the dried biomass with an organic solvent,
   separating the solid mass from the suspension obtained by treating the dried biomass with an organic solvent, and
   evaporating the resulting clear solution to form a polymeric film containing poly-β-hydroxyoctanoic acid,
the improvement which comprises selecting said organic solvent from the group consisting of acetone, methylisobutylketone, diisopropylketone, diethylketone, ethyl acetate, propyl acetate, butyl acetate, diethyl ether, diisopropyl ether, and tetrahydrofuran.

* * * * *